United States Patent
Bruder et al.

(10) Patent No.: US 8,189,734 B2
(45) Date of Patent: May 29, 2012

(54) SCANNING AND RECONSTRUCTION METHOD OF A CT SYSTEM AND CT SYSTEM

(75) Inventors: Herbert Bruder, Höchstadt (DE); Thomas Flohr, Uehlfeld (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/686,413

(22) Filed: Jan. 13, 2010

(65) Prior Publication Data

US 2010/0177862 A1    Jul. 15, 2010

(30) Foreign Application Priority Data

Jan. 14, 2009 (DE) .......................... 10 2009 004 580

(51) Int. Cl.
*A61B 6/00* (2006.01)
(52) U.S. Cl. .................................. 378/4; 378/8
(58) Field of Classification Search ............... 378/4, 8
See application file for complete search history.

(56) References Cited

U.S. PATENT DOCUMENTS

| | | | | |
|---|---|---|---|---|
| 4,503,461 A * | 3/1985 | Nishimura | ............... | 378/98.12 |
| 4,729,100 A * | 3/1988 | Tsujii | ............... | 378/4 |
| 5,262,946 A * | 11/1993 | Heuscher | ............... | 378/15 |
| 5,671,263 A * | 9/1997 | Ching-Ming | ............... | 378/8 |
| 5,761,267 A * | 6/1998 | Besson | ............... | 378/4 |
| 5,841,890 A * | 11/1998 | Kraske | ............... | 382/131 |
| 5,953,388 A * | 9/1999 | Walnut et al. | ............... | 378/4 |
| 6,005,917 A * | 12/1999 | Andersson et al. | ............... | 378/98.12 |
| 6,236,705 B1 * | 5/2001 | Stergiopoulos et al. | ............... | 378/8 |
| 6,574,300 B1 * | 6/2003 | Florent et al. | ............... | 378/19 |
| 6,937,690 B2 * | 8/2005 | Bruder et al. | ............... | 378/15 |
| 7,664,227 B2 * | 2/2010 | Speller et al. | ............... | 378/95 |
| 7,889,901 B2 * | 2/2011 | Bontus et al. | ............... | 382/128 |
| 2002/0154728 A1 * | 10/2002 | Morita et al. | ............... | 378/4 |
| 2003/0103595 A1 * | 6/2003 | Raupach | ............... | 378/4 |
| 2004/0258194 A1 * | 12/2004 | Chen et al. | ............... | 378/4 |
| 2005/0169420 A1 * | 8/2005 | Edic et al. | ............... | 378/4 |
| 2007/0198203 A1 * | 8/2007 | Kimura | ............... | 702/85 |
| 2008/0294038 A1 * | 11/2008 | Weese et al. | ............... | 600/431 |
| 2009/0161820 A1 | 6/2009 | Raupach | | |
| 2009/0161935 A1 | 6/2009 | Bruder | | |

FOREIGN PATENT DOCUMENTS

DE    102007061934 A1    6/2009

\* cited by examiner

*Primary Examiner* — Alexander H Taningco
(74) *Attorney, Agent, or Firm* — Harness, Dickey & Pierce, P.L.C.

(57) ABSTRACT

A method is disclosed for scanning an examination object with a CT system and the generation of at least one computed tomographic sectional view from data obtained from the scanning and a CT system. In at least one embodiment, data used for generating the at least one sectional image is filtered out with different intensities as a function of a predetermined time range and/or projection angle range of the measurement of high local frequencies.

32 Claims, 7 Drawing Sheets

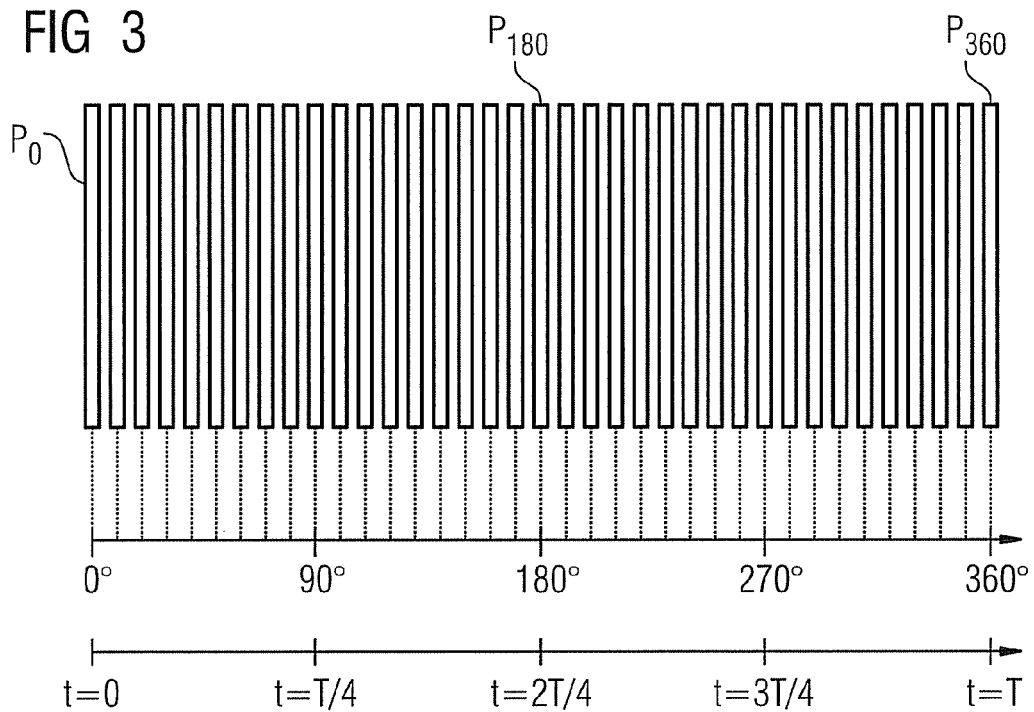
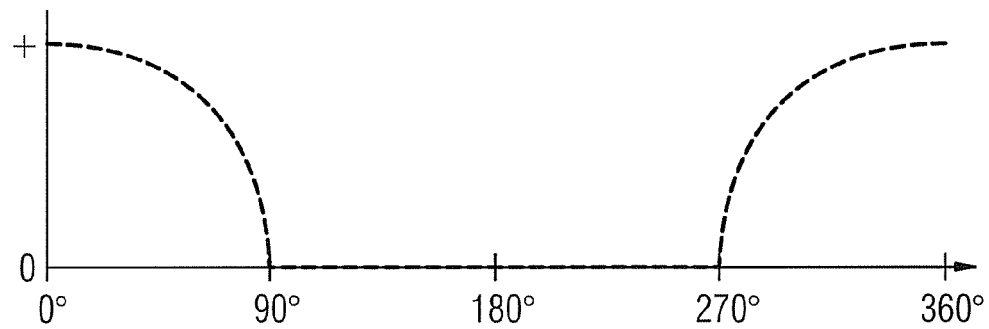
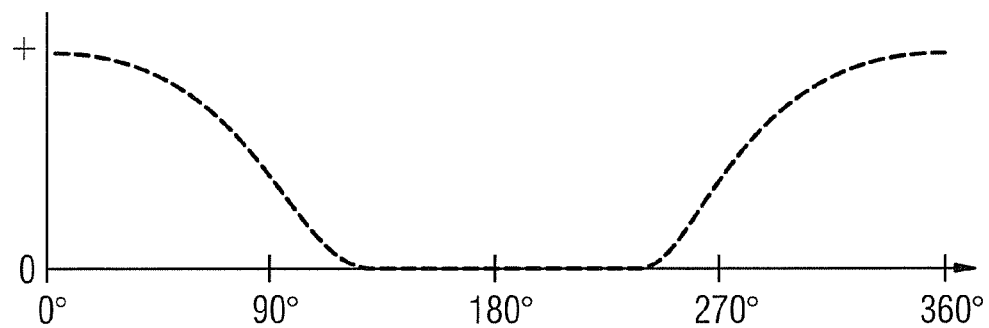

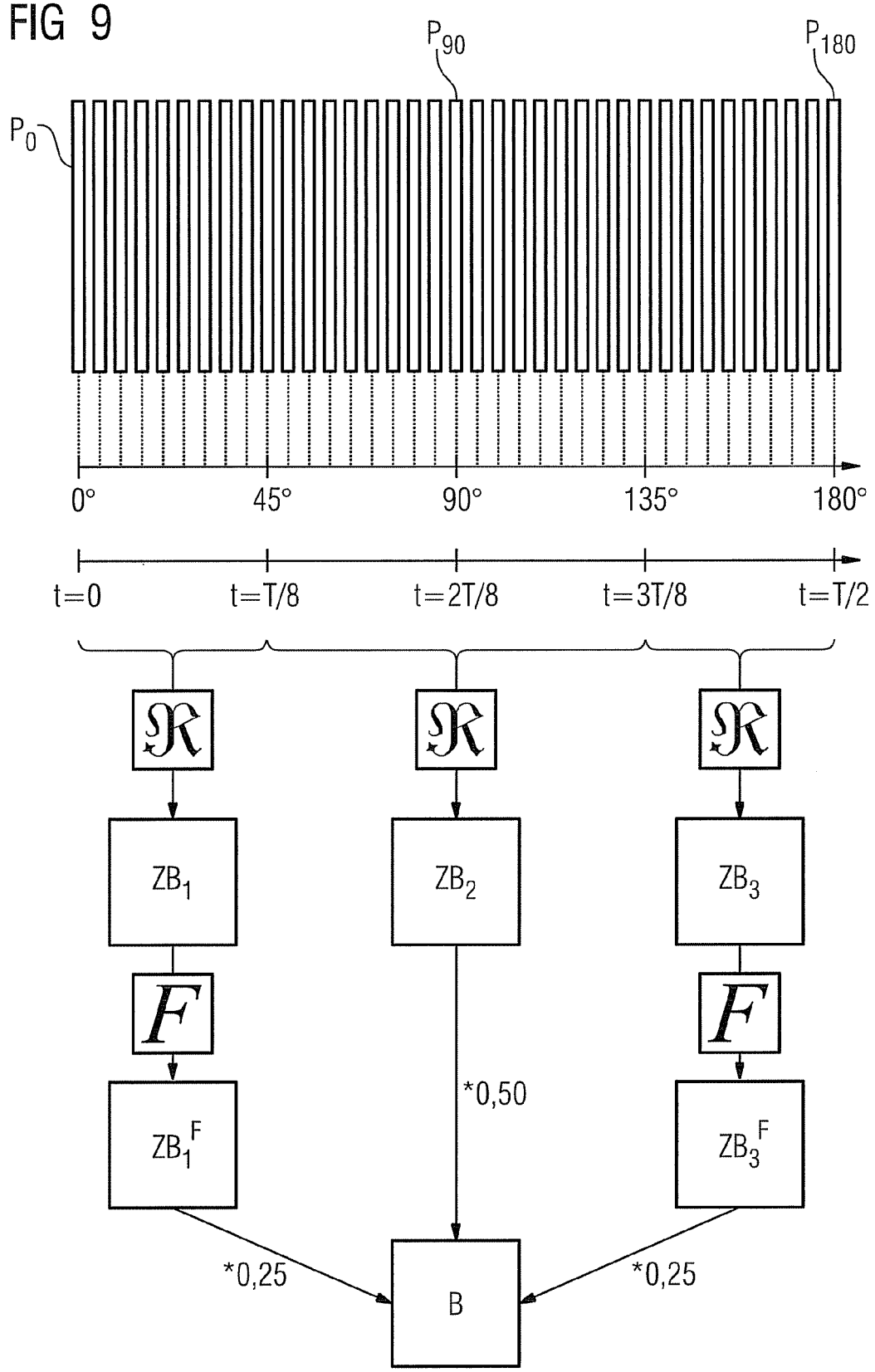

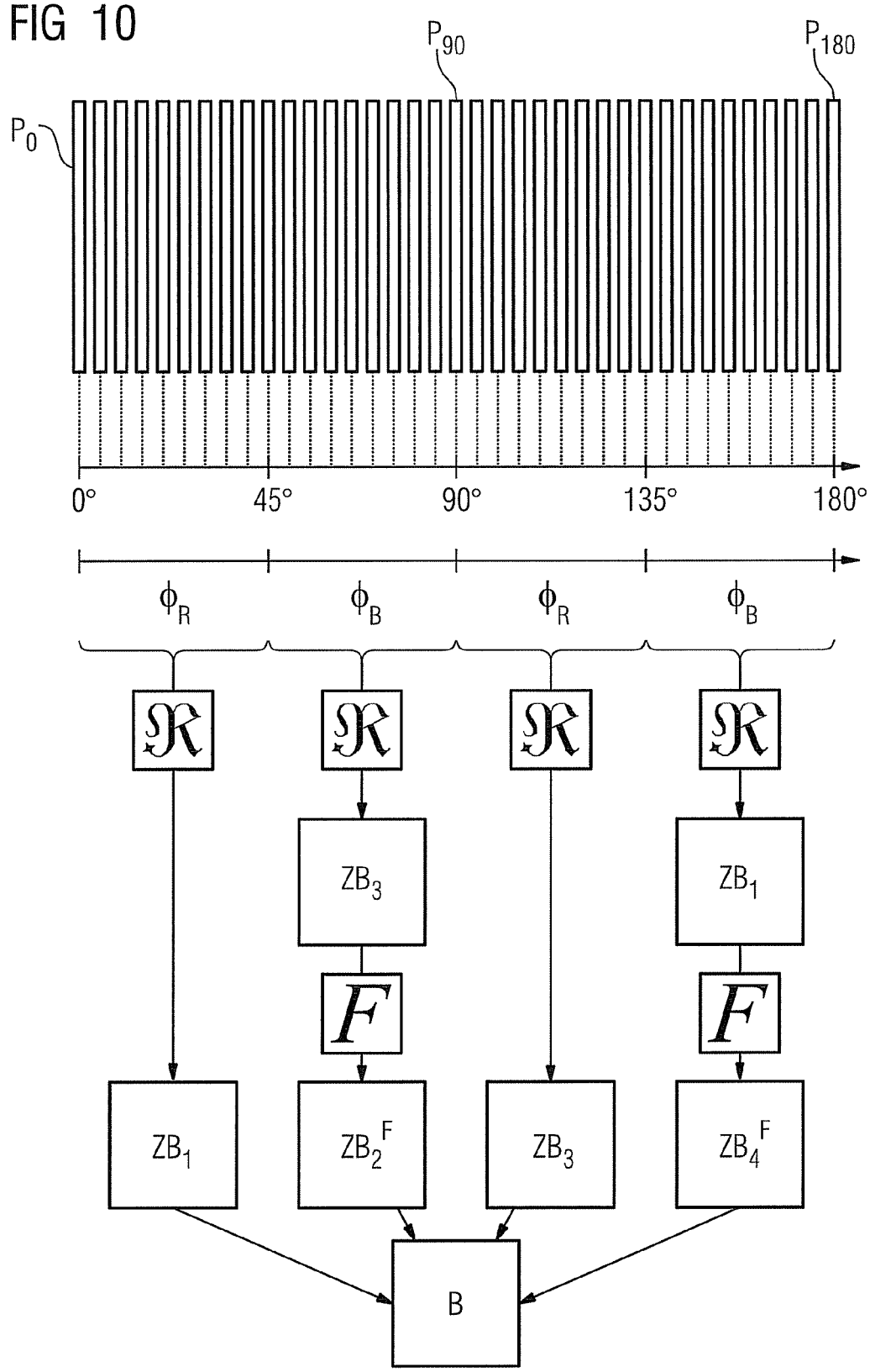

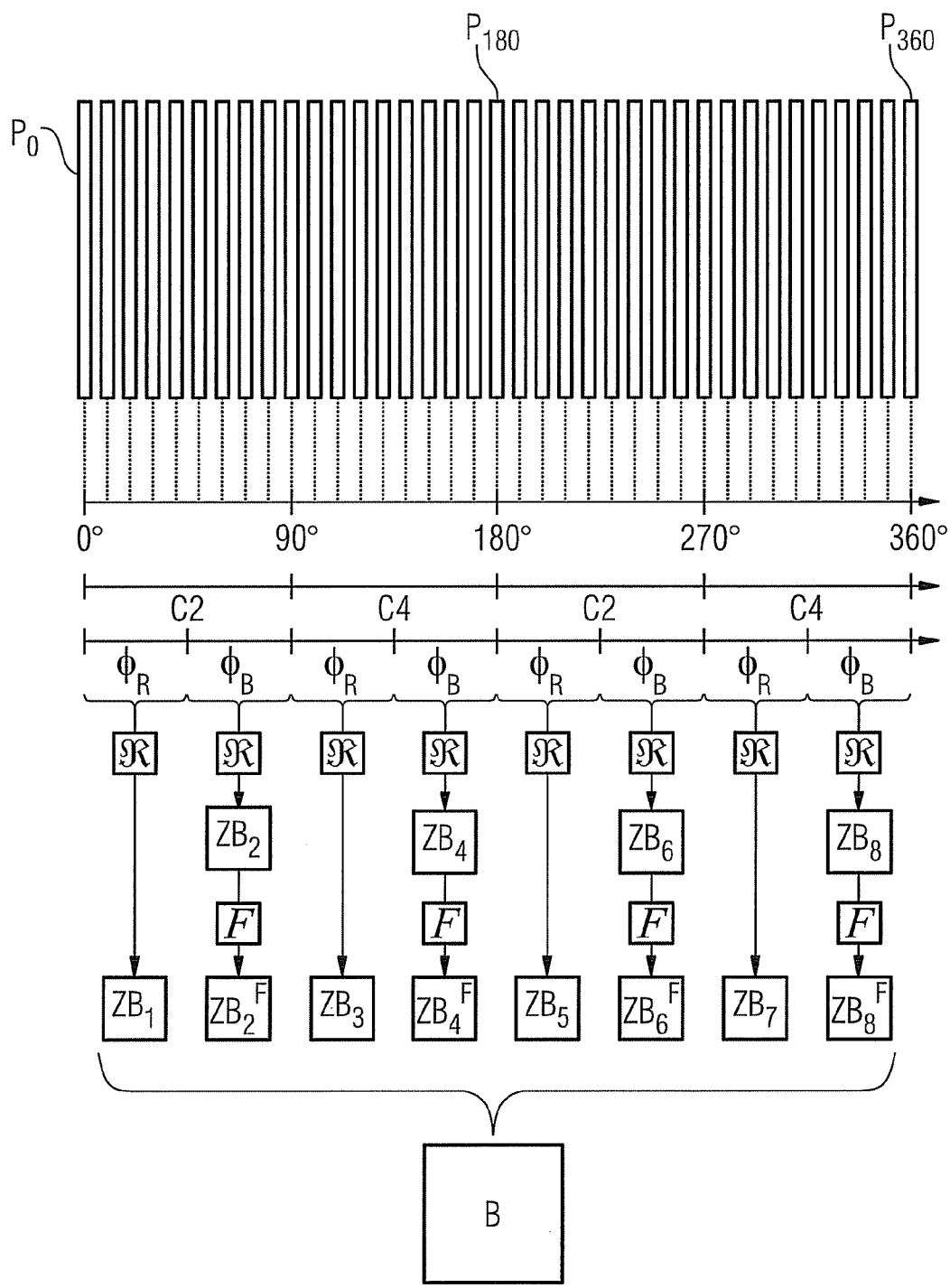

SCANNING AND RECONSTRUCTION METHOD OF A CT SYSTEM AND CT SYSTEM

PRIORITY STATEMENT

The present application hereby claims priority under 35 U.S.C. §119 on German patent application number DE 10 2009 004 580.5 filed Jan. 14, 2009, the entire contents of which are hereby incorporated herein by reference.

FIELD

At least one embodiment of the invention generally relates to a method for scanning an examination object with a CT system and the generation of at least one computed tomographic sectional view from the data obtained from the scanning. In addition, at least one embodiment of the invention also generally relates to a CT system, which is equipped to carry out this method.

BACKGROUND

In general, methods for scanning an examination object with a CT system are well known. In this case, for example circular scans, sequential circular scans with feed or spiral scans are used. In the case of these scans, absorption data of the examination object is recorded by means of at least one x-ray source and at least one detector opposite it from different recording angles and the absorption data collected in this way is calculated by means of appropriate computing methods into sectional views through the examination object. Well known reconstruction methods are for example filtered back projection (FBP), in the case of which the projections are transferred to a Fourier chamber where a filtering is carried out and subsequently after the back transformation of the data, a back projection takes place on the sectional view plane.

As another method, mention can for example be made of the SMPR method (SMPR=segmented multiple plane reconstruction), in the case of which incomplete intermediate images are reconstructed from projection data over circular segments of smaller than 180°, which are subsequently combined into complete sectional views, while it must be noted that the total projection data used in this case must be complementary to 180° projection data or 360° projection data.

A disadvantage of these generally known calculation methods resides in that in the case of a moving examination object, or an at least partially moving examination object, a lack of definition due to movement may occur in the image, because there may be, during the time of a scanning process for the data required for an image, a local displacement of the examination object or a part of the examination object, so that the base data, that leads to an image, does not reflect the whole spatially identical situation of the examination object. This problem of a lack of definition due to movement occurs particularly strongly when cardio CT examinations are carried out on a patient, in which because of the movement of the heart, a strong lack of definition due to movement may occur in the heart area or for examinations in which relatively fast changes in the examination object are to be measured.

SUMMARY

In at least one embodiment of the invention is directed to providing a method in the case of which the time resolution of the calculated computed tomographic sectional views is improved.

In at least one embodiment, the inventors found that it is possible to carry out, based both on raw data or projection data and on image data, high-pass filtering of the data used with an intensity that differs as a function of the time so that for the generation of a sectional view, data portions of high frequency—which carry the information for a lack of definition which occurs due to movement—come from one "core area", which corresponds to a relatively small period of time, whereas the further additional data of these portions of high frequency, necessary for a complete reconstruction of an image, are released and in this way only make a small or no contribution to it in order to produce a lack of definition due to movement in the image. In other words: by filtering out high-frequency data portions—from incomplete image data or projection data—from data which arises relatively distant with respect to time from a predetermined datum, and leaving the high-frequency data portions in data which arises relatively close to the predetermined datum with respect to time, with the subsequent calculation of sectional views from this partially high-pass filtered data, sectional views are obtained, the time resolution of which is improved compared with the sectional views from completely unfiltered data.

However, it is pointed out that by improving the time resolution, a reduction in the local resolution accompanies it at the same time. Data within the meaning of embodiments of the invention, which is partially high-pass filtered, can be both projection data and also incomplete image data, whereby it should be noted that both the treated projection data and the incomplete image data in each case arises from narrower time ranges than the total data, which is used for the calculation of the image.

If a scan of a patient within the framework of a cardio examination is for example considered in the case of a method based on projection data, it is possible that a multiline CT data record from a sequence scan or a spiral scan acquired in "fan-beam" geometry can be rebinned linewise in parallel geometry. For the phase-accurate reconstruction of the layer of an image, the 180° segment of the angle is then selected at the correct time and at the exact place. Every (two-dimensional) projection from the reconstruction segment undergoes Fourier transformation in lines. In accordance with the Fourier slice theorem, one obtains for each detector line the projection of the Fourier transformation of the attenuation coefficient in the selected projection direction. If the data of the 180° reconstruction area transformed in this way is now filtered for different angles with convolution kernels of different sharpness, then by selecting the convolution kernels in accordance with the invention it is possible for high frequencies to be omitted in the case of angle ranges at the start and/or at the end of the reconstruction area. In this process, the local definition is adversely affected, but the time resolution is improved in the considered layer of an image.

In the case of an application based on an image, a time series of partial scan images (=incomplete intermediate images in the case of the SMPR method) can be reconstructed for a selected heart phase and a system axis position. Each of these images contains projection data from a reconstruction area of the length of <180°. The total length of the time series must at least extend over 180°. Each of these images can now be Fourier-transformed in two dimensions. In one part of the time series, an upper frequency band can be omitted and the incomplete intermediate images calculated at different points in time can subsequently be combined into a final intermediate image. After the inverse Fourier transformation, the local definition is reduced, but the time resolution is increased at the same time. The time resolution and the local definition can be adjusted by setting suitable parameters.

In this way—both in an embodiment of the method based on the projection data and on the image data—the time resolution and the local definition can be influenced in a corresponding manner by changing the convolution kernel in accordance with an embodiment of the invention. On the basis of the mutual influencing of both the time and the local lack of definition, it can also be favorable to make available to the operating staff, in particular an adjudged doctor, an adjustment possibility—for example in the form of a slide control or a rotating control—by means of which the data can be influenced by the function of the time filtering and/or the determining of a focal point of minimal influencing and/or the determining of the span of the time range can be controlled with minimal influencing, it being possible that after each re-adjustment of these parameters, an immediate recalculation and display of at least one sectional view takes place.

In accordance with this above-described basic idea, the inventors propose, in at least one embodiment, a method for scanning an examination object with a CT system and the generation of at least one computed tomographic sectional view from the data determined from the scan, it being possible that in accordance with the invention in the case of data which is used for generating the at least one sectional view, as a function of a predetermined time range and/or a projection angle range of the measurement, high local frequencies can be filtered out with an intensity that differs.

According to the knowledge of the inventors that the data, which leads to a lack of definition due to movement in a reconstructed image, lies in essence within the range of high local frequencies, the measured data can in this way, in a relatively limited time range or according to the scanning method using radiation sources that rotate around the examination object in a limited projection angle range, be left largely unchanged, while in the boundary areas of this predetermined time range, high local frequencies are filtered out more strongly so that overall an improved time resolution of the determined sectional view is brought about. This basic idea can be used for both the projection data and the image data of incomplete intermediate images, which arise from a relatively narrow time range or a projection angle range.

In this case, it is explicitly pointed out that the time-phase-dependent high-pass filtering in accordance with the invention does not relate to filtering as is used in an FBP reconstruction method.

With regard to the application of the method in accordance with at least one embodiment of the invention on projection data level, it is proposed that this method in accordance with the invention has the following method steps:

scanning an examination object by means of at least one source of radiation out of a plurality of recording angles, collecting projection data over a predetermined projection angle range around the examination object, filtered back projection of the projection data to form a sectional view.

In the case of this method based on the projection data in accordance with at least one embodiment of the invention, in the projection data used per sectional plane as a function of the time range or the projection angle range of the measurement, high local frequencies with an intensity that differs are filtered out.

In this case, it is pointed out that in the case of a circular scan, each sectional plane must be equated with each line with regard to the detector lines, whereas in the case of a spiral scan, because of continuous feeding of the detector using gradual rotation, a line jump with regard to the detector can also take place.

In at least one embodiment, the inventors furthermore propose that the filtered back projection takes place using the projection data differently prefiltered as a function of time in accordance with at least one embodiment of the invention. By way of this clear separation of the filtering, the method can be inserted very easily into existing computing algorithms. However, it is also possible in the case of a correspondingly higher programming effort, to integrate the time-dependent high-pass filtering into the filtering of the filtered back projection and thus, if necessary, to save on additional computing steps, which has a favorable effect on the required computing time.

According to the known different methods for reconstruction, which can take place both on fan projection data and on parallel projection data, the high-pass filtering can also take place on the fan projection data or on the parallel projection data. A filtering on fan projection data indeed has the advantage that for each fan projection, there is an unambiguous point in time for measuring, whereas for parallel projection data no unambiguous point in time for measuring can be determined, because the parallel projection data is obtained from a rotation over a certain circular segment and for this reason from a finite time range. Should the high-pass filtering be carried out on fan projection data, a fan beam reconstruction need not follow absolutely. It is also possible in this case, with the fan projection data that has already been filtered in accordance with the invention, to carry out a rebinning to parallel data so that the actual reconstruction can take place on parallel projection data.

The method in accordance with at least one embodiment of the invention can be used both with projection data, which is present over a projection angle range of 360°, and with projection data, which is present over a projection angle range of 180°—as is mostly the case during cardio recordings.

Over and above that, the normal time curve can serve for the function of the time of the intensity of the high-pass filtering. However, should the method be used in the range of cardio examinations, then the normal time sequence is not considered as the time axis for the dependence of the intensity of the high-pass filtering, but the progress of the heart phase, it being possible that this progress can be considered independently from the heart cycle. In this way, projection data from a plurality of consecutive heart cycles can be used.

A typical process sequence for a cardio CT examination in accordance with at least one embodiment of the invention is then as follows:

scanning a patient with a beating heart by means of at least one source of radiation from a plurality of recording angles, collecting projection data over a predetermined projection angle range and in a predetermined heart phase area, if necessary across heart cycles, heart-phase-dependent filtering of the projection data with regard to high local frequencies, filtered back projection of the projection data to form a sectional view.

As mentioned before, the reconstruction method can also be used for the method in accordance with at least one embodiment of the invention, in the case of which a plurality of incomplete tomographic intermediate images occur, that can be assigned to certain projection angle ranges or certain measuring times, with regard to the absolute time axis or with regard to a heart phase, it being possible that the filtering out of high local frequencies in this case only takes place on the plane of the intermediate images.

A scanning and reconstruction method based on an image is thus proposed in at least one embodiment, in the case of which the following method steps are carried out:

scanning an examination object by means of at least one source of radiation from a plurality of recording angles, collecting projection data over an entire projection angle range around the examination object, reconstructing at least two incomplete tomographic intermediate images out of projection angle partial areas that are complementary to each other relative to the entire projection angle range, and combining the at least two incomplete intermediate images into one complete sectional view, it being possible that in accordance with the invention before the combination of the intermediate images from the at least two incomplete intermediate images high local frequencies are filtered at different intensities.

Because the intermediate images that occurred in the method described above can also be assigned to different temporal scanning ranges, it is now possible to leave a certain narrow time range largely untouched with regard to the high local frequencies, while intermediate images from another scanning time range are deprived of their high local frequencies, so that from this time range no information that could produce the lack of definition due to movements can be transferred to the final sectional view combined at a later stage from the individual intermediate images, and in this way the lack of definition due to movement in the final sectional view is reduced.

For the high-pass filtering of the intermediate images, these can for example be Fourier-transformed in a frequency chamber, where the filtering of high frequencies takes place and are then transformed back into the local chamber, so that the combination into a final sectional view is made possible. As an alternative, instead of a Fourier transformation, a wavelet transformation of the intermediate images can also take place, whereby the high-pass filtering is carried out on the basis of the wavelets and these are subsequently transformed back for further processing.

The reconstruction of the intermediate images can take place both on the basis of fan projection data or on the basis of parallel projection data, whereby a reconstruction on the basis of fan projection data makes possible a more unambiguous temporal assignment of the intermediate images.

Analogously to at least one embodiment of the method based on projection data, to form the at least one sectional view, intermediate images from either a projection angle range of 180° or a projection angle range of 360° can be used.

Should the method in accordance with at least one embodiment of the invention be used in the ambit of a cardio examination, it is proposed that the time range for the dependence of the intensity of the high-pass filtering refers to the progress of the heart phase independent of the heart cycle, whereby the projection data used for the intermediate images can be obtained from at least two consecutive heart cycles.

It is pointed out in addition that the scanning of the examination object can be carried out by way of a single radiation source or by way of at least two radiation sources rotating around the examination object. In addition, the at least one sectional view, which was generated in accordance with the above-described method, can be stored for further processing and/or shown visually on an output unit.

At least one embodiment of the invention includes, in addition to the method described above, also a CT system with a control unit and a computing unit in order to control the CT system, detector data acquisition and the reconstruction of tomographic sectional views, comprising a program memory for storing program code in so far as the control unit and the computing unit in the memory also contain program code, which carries out the method described above during operation.

BRIEF DESCRIPTION OF THE DRAWINGS

The invention is described in more detail below on the basis of the example embodiments with the help of figures, wherein only the features necessary for understanding the invention are shown. The following reference characters, abbreviated designations and variables are used: C1: x-ray CT system; C2: first X-ray tube; C3: first detector; C4: second X-ray tube (optional); C5: second detector (optional); C6: gantry housing; C7: C arm; C8: movable patient table; C9: system axis; C10: control unit and computing unit; C11: contrast medium injector; C12: lead for ECG derivation; B: final sectional view; F: filtering; $Prg_1$ to $Prg_n$: program code; $P_0$ to $P_{360}$: projections between 0 and 360° in a sectional plane; $\Re$: reconstruction; T: rotation time of an x-ray emitter about 360°; t: time; $ZB_1$ to $ZB_8$: incomplete intermediate images; $ZB_i^F$: high-pass filtered incomplete intermediate images; $\phi_R$: rest phase in the heart cycle; $\phi_B$: movement phase in the heart cycle.

These are as follows:

FIG. 3: Schematically represented projection data of a sectional view over a projection angle of 360°;

FIG. 4: Schematic representation of a time-dependent or projection-angle-dependent intensity of the high-pass filtering of the projection data from FIG. 3;

FIG. 5: Schematic representation of another time-dependent or projection-angle-dependent intensity of the high-pass filtering of the projection data from FIG. 3;

FIG. 9: Schematically represented sequence of a sectional view calculation with image-based time-dependent high-pass filtering from projection data of a sectional view over a projection angle of 180° with an SMPR method;

FIG. 10: Schematically represented sequence of a sectional view calculation with an image-based time-dependent and heart-phase-dependent high-pass filtering from projection data of a sectional view over a projection angle of 180° with an SMPR method in the case of a cardio examination;

FIG. 11: Schematically represented sequence of a sectional view calculation with an image-based time-dependent and heart-phase-dependent high-pass filtering from projection data of a sectional view over a projection angle of 360° with an SMPR method in the case of a cardio examination.

DETAILED DESCRIPTION OF THE EXAMPLE EMBODIMENTS

Figure 1:
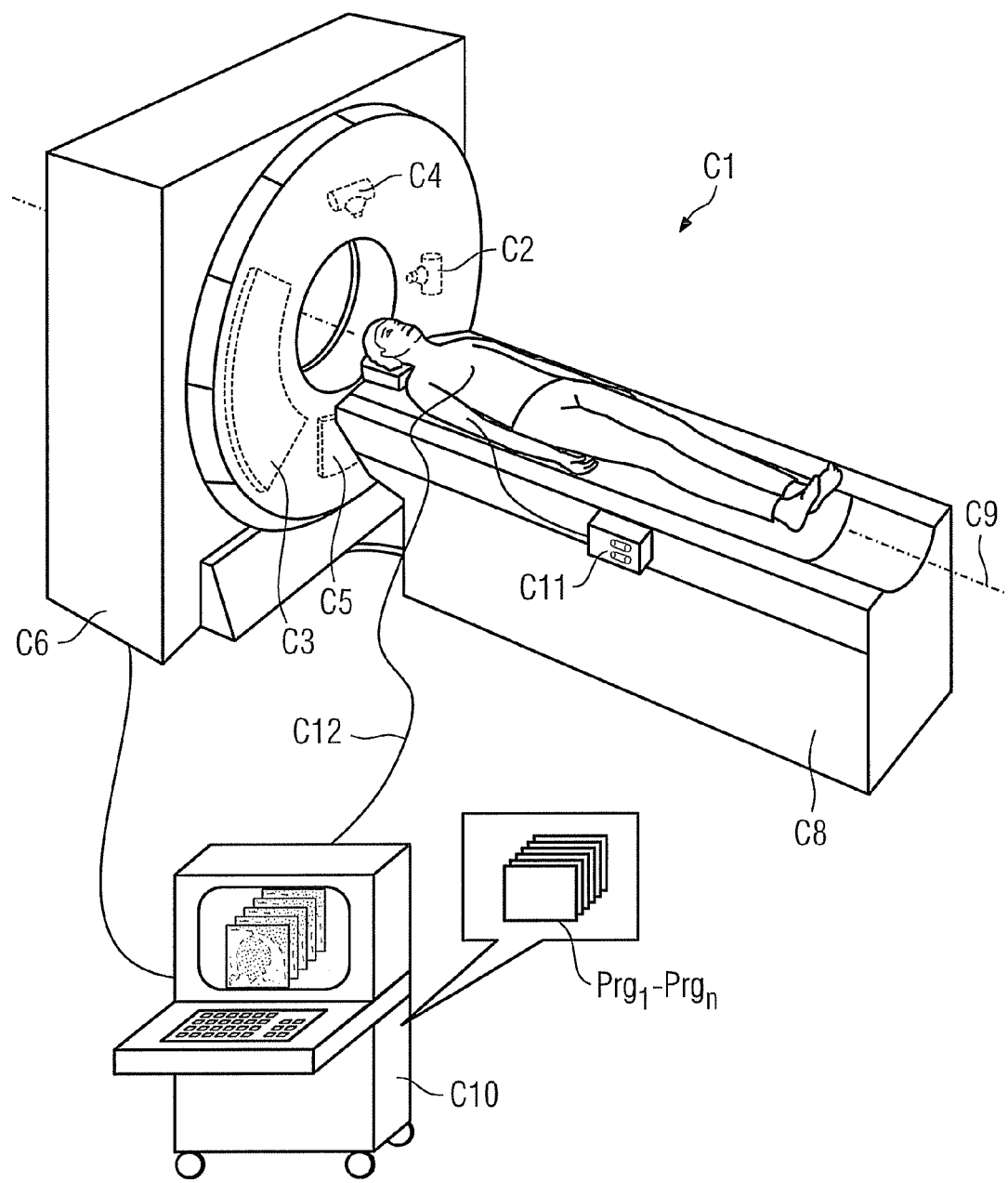
FIG. 1: CT system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 2:
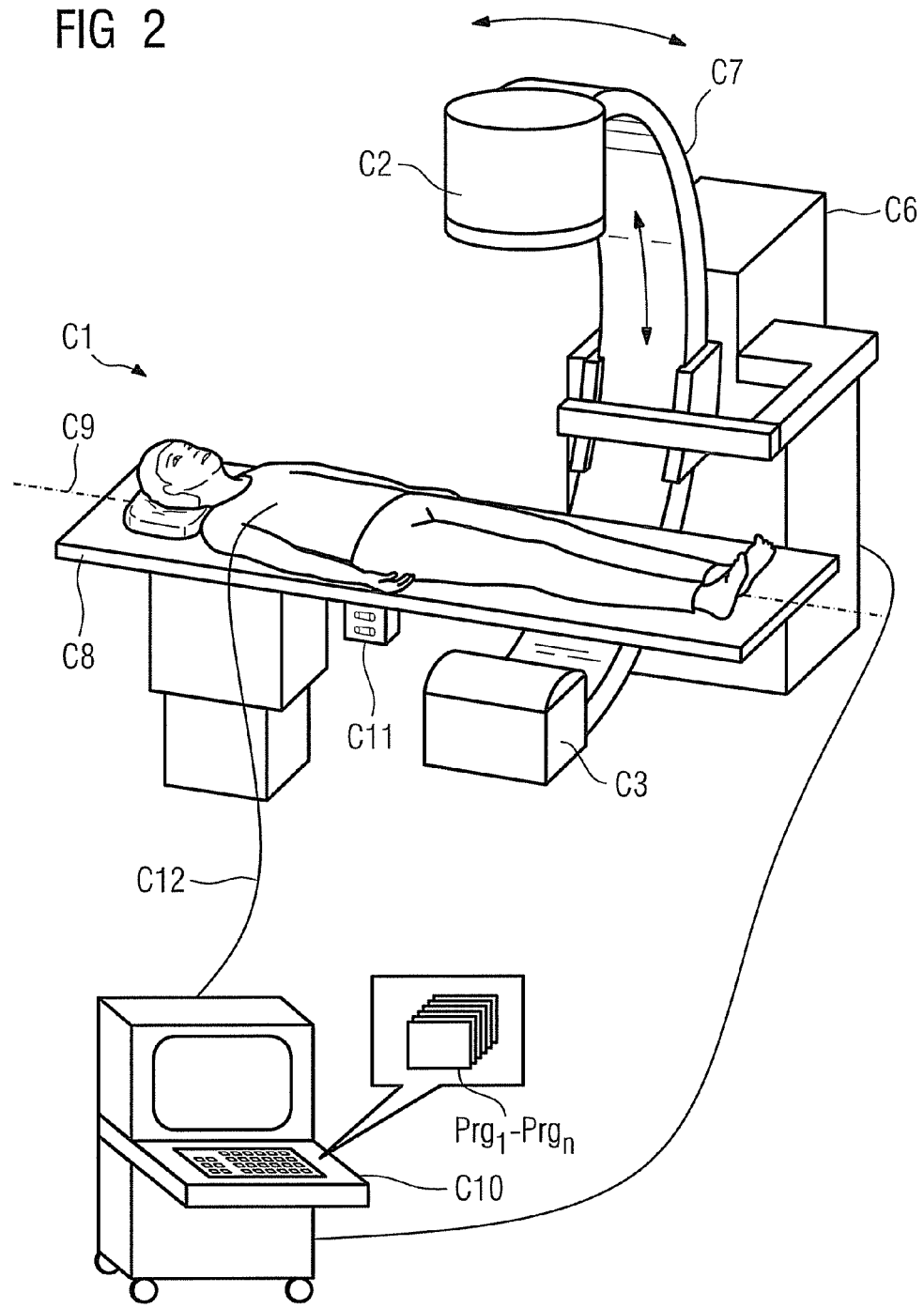
FIG. 2: C-arm system.

The method in accordance with an embodiment of the invention can be carried out both with CT systems with gantry as shown for example in FIG. 1 and with C-arm systems, as shown in FIG. 2.

FIG. 1 shows a CT system C1 with a gantry housing C6, in which there is a closed gantry not shown here on which a first x-ray tube C2 with a detector C3 on the opposite side are arranged. Optionally, in the CT system shown here, a second x-ray tube C4 is arranged with a detector C5 opposite it so that by means of the emitter/detector combination which have in addition been made available, a higher time resolution can be achieved, or when using different x-ray energy spectra in the emitter/detector systems, "dual energy" examinations can also be carried out. In addition, the CT system C1 has a patient table C8, on which, during the examination, a patient can be shifted along a system axis C9 into the measuring field, it being possible that the scan itself can even be carried out both as a pure circular scan without feed of the patient only in the relevant examination area. As an alternative, a sequential scan can be carried out in the case of which the patient is shifted stepwise between the individual scans through the examination field. As an alternative, it is also possible of course to carry out a spiral scan in which the patient is shifted continuously during the rotating scan with the X-radiation along the system axis C9 through the examination field between x-ray tube and detector. The present CT system is controlled by way of a control and computing unit C10 with a computer program code $Prg_1$ to $Prg_n$, which is present in a memory. In addition, said control and computing unit C10 can also carry out the function of an ECG, whereby a lead C12 is used for deriving the ECG potentials between a patient and the control and computing unit C10.

By way of this additional ECG examination, the heart activity of the patient can for example be determined and on the basis of the knowledge of the current heart phase during the scanning and the assigning of the measured values in a known manner, only those measured data can be used that are in certain heart phases, in which as slight as possible lack of definition due to movement can be expected.

In addition, the CT system C1 shown in FIG. 1 also has a contrast medium injector C11 by which additional contrast medium can be injected into the blood circulation of the patient so that the blood vessels of the patient, in particular the hear chambers of the beating heart, can be shown more clearly. In addition, it is also possible in this case to carry out perfusion measurements, for which an embodiment of the proposed method is likewise suitable.

FIG. 2 shows a C-arm system, in the case of which contrary to the CT system from FIG. 1, the housing C6 carries the C-arm C7, to which on the one hand the x-ray tube C2 and on the other hand, the detector C3 on the opposite side are secured. For scanning, the C-arm C7 is likewise swiveled around a system axis C9 so that scanning can take place from a plurality of detection angles and corresponding projection data can be determined from a plurality of projection angles. The C-arm system C1 has by the same token as the CT system from FIG. 1, a control and computing unit C10 with computer program code $Prg_1$ to $Prg_n$. In addition, it is possible that by means of this control and computing unit C10 and with the aid of an ECG lead C12, an ECG derivation of the heart can also be carried out and by means of the control and computing unit C10, a contrast medium injector C11 can also be controlled, which can administer an injection with a contrast medium in the desired form to a patient on the patient table C8.

Because in the case of both tomographic x-ray systems shown, the same computing methods can basically be used to generate sectional views, the method in accordance with an embodiment of the invention can also be used for both systems.

In accordance with the method in accordance with an embodiment of the invention described above, it is essential to subject data obtained from scanning a patient, as a function of the point in time or the time range of its establishment, to a high-pass filtering of different intensities. Thus data arising from a narrow time range can largely remain unchanged, whereas data which is not from this narrow unchanged time range is subjected to intense high-pass filtering. As a result of this high-pass filtering, image or projection data portions are removed, which are responsible for the lack of definition due to movement of the finally generated image, so that by means of its removal a better time resolution of the final image is produced. This method can be carried out both on raw data or projection data or it can be carried out on intermediate images, whereby the requirement for this is that the intermediate images are provided with the same time stamps or similar related time stamps with regard to the data on which these are based.

An example of such a raw-data-based or a projection-data-based filtering is shown in FIGS. 3 to 5.

FIG. 3 shows schematic projections $P_0$ to $P_{360}$ of a predetermined sectional plane, which is used for the reconstruction of an image at a later stage. Should it concern, in the scan used here as a basis, a circular scan, then the projection data shown here corresponds to the projection data of a certain detector line. Should a spiral scan take place, the projection data shown here corresponds to the projections at a certain coordinate of the system axis, i.e. a specific z-coordinate. In this case, it is possible that on the basis of the feed, during the spiral scan, absorption data is used from a plurality of lines. The correspondingly continuous scan angles between 0 and 360° are shown on the abscissa. In addition, an abscissa is also shown, in which the time curve between t=0 to t=T, whereby T corresponds to the rotation time for a full rotation of a scanning system around the examination object, is plotted.

Should a reconstruction method be used as the starting point, in the case of which the projection data of a full rotation, i.e. over projection angles from 0 to 360°, should be used and should however at the same time a method within the meaning of an embodiment of this invention be used to improve the time resolution, then it is possible to filter the projection data $P_0$ to $P_{360}$ shown in FIG. 3 according to its scanning angle or according to its measuring time in a different manner with regard to higher frequencies, whereby the intensity of the high-pass filtering should be in the desired period under examination—here for example the time between t=T/4 and t=3T/4.

In FIG. 4, an example of such a filter curve is shown. The dotted line should represent the expression of the high-pass filtering—plotted on the ordinate—whereas the abscissa corresponds to FIG. 3. Accordingly, in the case of a projection angle of 0°, a relatively intense high-pass filtering takes place, which weakens up to a projection angle of 90°. The projection data is not filtered in the range between 90 and 270°, while from 270° to 360° the high-pass filtering is intensified with regard to its expression.

As an alternative, another example curve of the intensity of the high-pass filtering over the range from 0 to 360° is shown in FIG. 5, whereby smoother transitions are used in this case between the core area and the boundary area.

Figure 6:
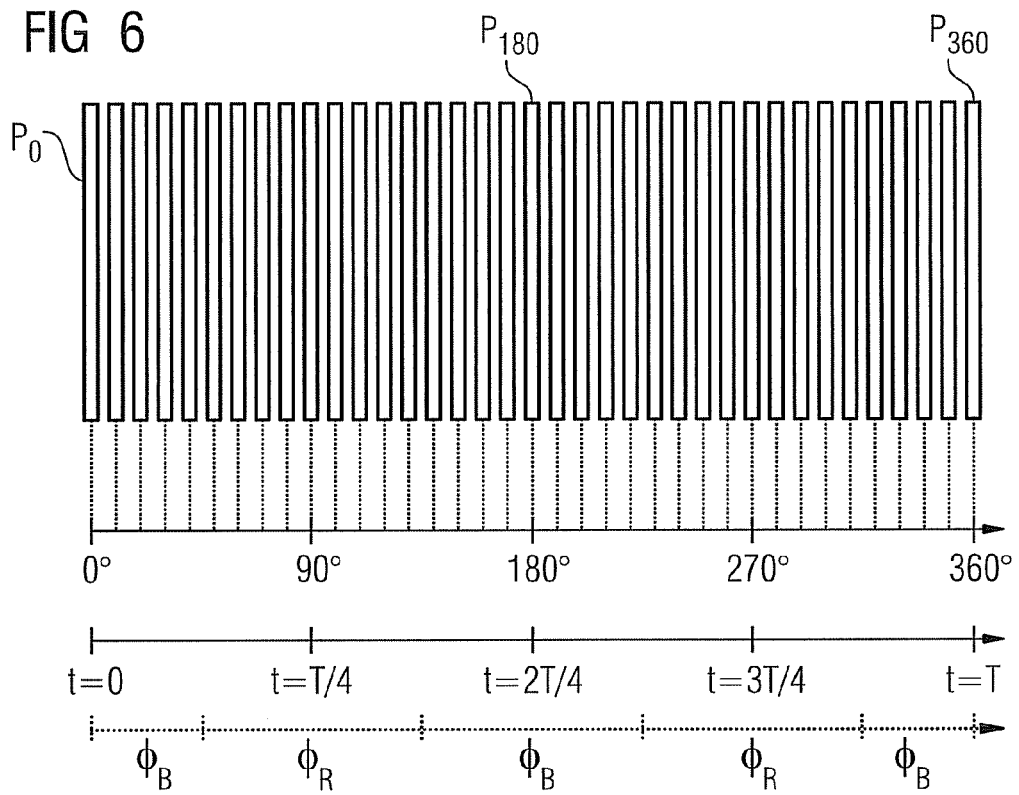
FIG. 6: Schematically represented projection data of a sectional view over a projection angle of 360°.
Figure 7:
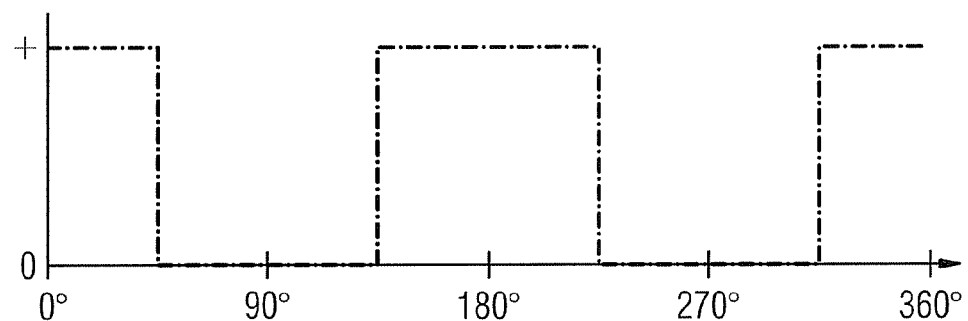
FIG. 7: Schematic representation of a time-dependent or projection-angle-dependent intensity of the high-pass filtering of the projection data from FIG. 6.
Figure 8:
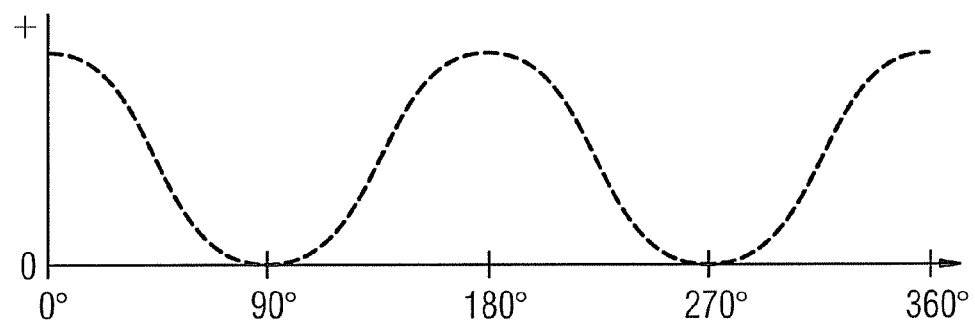
FIG. 8: Schematic representation of a further time-dependent or projection-angle-dependent intensity of the high-pass filtering of the projection data from FIG. 6.

A similar variant of the method in accordance with an embodiment of the invention is shown in FIGS. 6 to 8, whereby likewise a reconstruction of projection data takes place over 360°, though a cyclical movement of the examination object is used as a basis in this case, which takes place in a synchronized manner with the rotation time of the scanning. Should the synchronization be configured in such a way that for example in the range between 45 and 135° a movement which is as small as possible in the examination object takes place, which again repeats itself at 225 to 315°, then a filtering can be carried out in the same way as is shown in FIGS. 7 and 8.

FIG. 6 corresponds to the representation of the projection data from FIG. 3, though another—dotted—abscissa is shown in addition, in which the movement phases of a cyclically moving examination object or a part of an examination object are indicated. In this process, a movement phase with a relative rest with $\phi_R$ (=rest phase) and a relative movement with $\phi_B$ (=moving phase) is indicated.

In FIG. 7, on the one hand, a rectangular curve (dash-dotted) of the filtering is shown, this means that the projection data, which ought to be filtered, is subjected to a gradual filtering, whereas the data from rest areas is not subjected to any filtering.

FIG. 8 shows a similar filter as is shown in FIG. 5, whereby the change of the filter in relation to the rotation of the scanning is adapted to the movement situation of the moving examination object.

Should the projection data from FIGS. 3 and 6 be subjected to a high-pass filtering in accordance with the invention, then this data can subsequently be used in all the known reconstruction methods and also for example in a filtered back projection.

As has already been described above, it is also possible to carry out the high-pass filtering in accordance with an embodiment of the invention for the elimination of the lack of definition due to movement on both fan projections and on parallel projections. In this case, it must be taken into consideration that in the case of parallel projections a less unambiguous temporal assignment of the parallel projections is possible.

Reference is made to the fact that only by way of the selection of a narrower time range, for which only high-frequency data portions are used in the reconstruction, is the time resolution improved. In addition, should this narrower time range be in a relative rest phase of a, if necessary, cyclically moving examination object, this effect of reduction of the lack of definition due to movement is again increased.

The method in accordance with an embodiment of the invention can also be used on image-based data in the same way as is shown for example in FIG. 9.

FIG. 9 on the other hand shows a plurality of projection data $P_0$ to $P_{180}$ over a projection angle range from 0 to 180°, corresponding to a scanning time range from t=0 to t=T/2, whereby T again corresponds to the rotation time of a complete rotation. In this image-based method, incomplete intermediate images $ZB_1$ to $ZB_3$ are now reconstructed from the projection data of specific time ranges or projection angle ranges. In this process, the intermediate images $ZB_1$ and $ZB_3$, which come from the ranges from 0 to 45° and 135 to 180°, are subjected to a high-pass filtering F so that from the intermediate images $ZB_1$, a filtered intermediate image $ZB_1^F$ or from the intermediate image $ZB_3$, the filtered intermediate image $ZB_3^F$ is obtained. In this case, the intermediate image $ZB_2$ from the projection range between 45 and 135° is not filtered. Subsequently, the known combination of the intermediate images into a final sectional view B takes place, whereby a weighting of the intermediate images can be carried out with weighting factors of 0.25 and 0.50 according to the projection angle range on which the intermediate images are based.

Reference is made to the fact that the method described in FIG. 9 can also be carried out over a projection angle range from 0 to 360°, whereby only the abscissas of FIG. 9 are compressed in a corresponding manner.

FIG. 10 describes the method in accordance with an embodiment of the invention in connection with a cardio reconstruction, whereby when selecting the time ranges which are subjected to a high-pass filtering, a relation is drawn to the heart phase. The intermediate images which are reconstructed in each case, the data of which comes from relatively non-moving heart phases $\phi_R$, are taken over without high-pass filtering, whereas reconstructed incomplete intermediate images, which come from the heart phases $\phi_B$ with a relatively strong movement are subjected to a high-pass filtering in accordance with an embodiment of the invention.

In addition, the method in accordance with an embodiment of the invention can also be used with a CT system with two or more emitter/detector systems, whereby the corresponding projection data, irrespective of its origin with regard to the emitter/detector systems, can be combined. Both the origin from different emitter/detector systems and the origin of data from different heart phases is shown schematically in FIG. 11 in the range of the abscissas shown with C2 and C4—the two X-ray tubes—or the different heart phases $\phi_R$ (=rest phase) and $\phi_B$ (=moving phase). A corresponding schematic curve of such a reconstruction of intermediate images from the corresponding rest phases or movement phases of the heart is shown schematically in this case, whereby the final sectional view in this example comes on the one hand from projection data over an angle area from 0 to 360° and can be combined in total from eight partially filtered intermediate images.

Of course the embodiments of method shown in this case for scanning with a plurality of emitter/detector systems can also be transferred to the previously depicted projection-data-based method.

It is evident that the above-mentioned characteristics of the invention can be used not only in the combination specified in each case, but also in other combinations or can be used alone without moving outside the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

List Of Reference Characters

C1 X-ray CT system
C2 first X-ray tube
C3 first detector
C4 second X-ray tube (optional)
C5 second detector (optional)
C6 gantry housing C7 C-arm
C8 movable patient table
C9 system axis
C10 control and computing unit
C11 contrast medium injector
C12 lead for ECG derivation
B final sectional view
F filtering
$Prg_1$ to $Prg_n$ program code
$P_0$ to $P_{360}$ projections between 0 and 360° in a sectional plane
$\Re$ reconstruction
T rotation time of an X-ray emitter around 360°
t time
$ZB_1$ to $ZB_8$ incomplete intermediate images
$ZB_i^F$ high-pass filtered incomplete intermediate images
$\phi_R$ rest phase in the heart cycle
$\phi_B$ movement phase in the heart cycle

What is claimed is:

1. A method for scanning an examination object with a CT system and generating at least one computed tomographic sectional view from data determined by the scanning, the method comprising:
   scanning the examination object for period of time corresponding to a range of projection angles;
   producing a time and projection angle dependent set of projection data including portions with low and high spatial frequencies;
   filtering the portions of the set of projection data including high spatial frequencies with different strengths based on the projection angle to reduce the portions of the set of projection data including high spatial frequencies with different strengths;
   calculating a new set of projection data based on the reduced portions of the set of projection data; and
   generating at least one computed tomographic sectional view using the new set of projection data.

2. The method as claimed in claim 1, further comprising:
   scanning the examination object by way of at least one source of radiation from a plurality of recording angles;
   collecting projection data over the projection angle range around the examination object; and
   filtered back projecting the collected projection data to form the sectional view.

3. The method as claimed in claim 2, wherein the filtered back projection takes place with the prefiltered projection data.

4. The method as claimed in claim 2, wherein the time-dependent high-pass filtering is integrated into the filtering of the filtered back projection.

5. The method as claimed in claim 2, wherein the high-pass filtering takes place on fan projection data.

6. The method as claimed in claim 5, wherein the reconstruction of the at least one sectional view takes place on fan projection data.

7. The method as claimed in claim 5, wherein the reconstruction of the at least one sectional view takes place on projection data parallelized according to the time-dependent high-pass filtering.

8. The method as claimed in claim 2, wherein the high-pass filtering takes place on parallel projection data.

9. The method as claimed in claim 2, wherein projection data is used over a projection angle range of 360°.

10. The method as claimed in claim 2, wherein projection data is used over a projection angle range of 180°.

11. The method as claimed in claim 2, wherein the normal time course is used as the time axis for the dependence of the strength of the high-pass filtering.

12. The method as claimed in claim 11, wherein the examination object is a patient, and a progress of a heart phase independent from a heart cycle of the patient is used as the time axis for the dependence of the strength of the high-pass filtering.

13. The method as claimed in claim 12, wherein the projection data used comes from at least two consecutive heart cycles.

14. The method as claimed in claim 2, further comprising:
   scanning the examination object by way of at least one source of radiation from a plurality of recording angles;
   collecting projection data over an entire projection angle range around the examination object;
   reconstructing at least two incomplete tomographic intermediate images from projection angle partial ranges that complement one another with regard to the entire projection angle range; and
   combining the at least two incomplete intermediate images into one complete sectional view, wherein, before combining the intermediate images from the at least two incomplete intermediate images, the high spatial frequencies are filtered out at different strengths.

15. The method as claimed in claim 14, wherein the strength of the high-pass filtering takes place as a function of the time range of the data projection data acquisition of the intermediate images.

16. The method as claimed in claim 14, wherein, before the high-pass filtering, the intermediate images are Fourier-transformed in a frequency chamber, filtered there and subsequently transformed back into the local chamber.

17. The method as claimed in claim 14, wherein, before the high-pass filtering, the intermediate images are trans-formed in wavelets, high-pass filtered and then trans-formed back into the local chamber.

18. The method as claimed in claim 14, wherein at least one of the intermediate images is not subjected to a high-pass filtering.

19. The method as claimed in claim 14, wherein the reconstruction of the intermediate images takes place with fan projection data.

20. The method as claimed in claim 14, wherein the reconstruction of the intermediate images takes place with parallel projection data.

21. The method as claimed in claim 14, wherein intermediate images are used from a projection angle range of 360° for the formation of the at least one sectional view.

22. The method as claimed in claim 14, wherein intermediate images are used from a projection angle range of 180° for the formation of the at least one sectional view.

23. The method as claimed in claim 14, wherein the normal time course is used as the time axis for the dependence of the strength of the high-pass filtering.

24. The method as claimed in claim 23, wherein the examination object is a patient and the time range for the dependence of the strength of the high-pass filtering refers to a progress of a heart phase independent of a heart cycle.

25. The method as claimed in claim 24, wherein the projection data used for the intermediate images comes from at least two consecutive heart cycles.

26. The method as claimed in claim 1, wherein the scanning of the examination object takes place by at least two radiation sources rotating around the examination object.

27. The method as claimed in claim 1, wherein the at least one sectional view is at least one of stored for further processing and shown visually on an output unit.

28. A CT system with a control and computing unit for controlling the CT system, detector data acquisition and reconstruction of tomographic sectional views comprising:

a program memory for storing program code which, during operation of the CT system, carries out a method as claimed in claim 1.

29. A method, comprising:
scanning an examination object by way of at least one source of radiation from a plurality of recording angles;
collecting projection data over a projection angle range around the examination object;
filtered back projecting the collected projection data to form a sectional view;
filtering portions of the projection data including high spatial frequencies with different strengths based on at least one of the recording angles to reduce the portions of the set of projection data including high spatial frequencies with different strengths;
calculating a new set of projection data based on the reduced portions of the set of projection data; and
generating at least one computed tomographic sectional view using the new set of projection data.

30. A non-transitory computer readable medium including program segments for, when executed on a computer device, causing the computer device to implement the method of claim 1.

31. A non-transitory computer readable medium including program segments for, when executed on a computer device, causing the computer device to implement the method of claim 2.

32. A CT system with a control and computing unit for controlling the CT system, detector data acquisition and reconstruction of tomographic sectional views comprising:
a program memory for storing program code which, during operation of the CT system, carries out a method as claimed in claim 2.

* * * * *